United States Patent [19]

Mader et al.

[11] Patent Number: 5,625,062

[45] Date of Patent: Apr. 29, 1997

[54] METHOD OF MAKING SOLUBLE SQUARAINE DYES

[75] Inventors: Roger A. Mader, Stillwater; William D. Ramsden, Afton; Terence D. Spawn, West Lakeland Township; Daniel E. Saddoris, Hastings, all of Minn.

[73] Assignee: Minnesota Mining and Manufacturing Company, St. Paul, Minn.

[21] Appl. No.: 654,651

[22] Filed: May 29, 1996

[51] Int. Cl.$^6$ ............................................. C07D 239/70
[52] U.S. Cl. ............................................. 544/249; 564/307
[58] Field of Search ............................................. 544/249; 564/307

[56] References Cited

U.S. PATENT DOCUMENTS

| | | | |
|---|---|---|---|
| 4,524,220 | 6/1985 | Law et al. | 564/307 |
| 4,525,592 | 6/1985 | Law et al. | 564/307 |
| 5,097,029 | 3/1992 | Shannon | 544/249 |
| 5,360,694 | 11/1994 | Thien et al. | 430/200 |
| 5,380,635 | 1/1995 | Gomez et al. | 430/517 |
| 5,550,156 | 3/1996 | Marder et al. | 252/582 |

*Primary Examiner*—Mukund J. Shah
*Assistant Examiner*—Pavanaram K. Sripada
*Attorney, Agent, or Firm*—Gary L. Griswold; Walter N. Kirn; Daniel C. Schulte

[57] ABSTRACT

The present invention provides a novel process for the production of organic solvent soluble squaraine dyes. More specifically, the invention describes how a difficult to prepare tetrahydroxy squaraine intermediate can be prepared in an organic solvent system in the presence of water. This intermediate can then be esterified in pyridine to form the soluble squaraine dye which can then be easily isolated from the reaction mixture. The invention also provides the dyes prepared according to this method.

20 Claims, No Drawings

METHOD OF MAKING SOLUBLE SQUARAINE DYES

FIELD OF THE INVENTION

The present invention provides a novel method for the production of organic solvent soluble squaraine dyes. More specifically, the invention describes how a difficult to prepare tetrahydroxy squaraine intermediate can be prepared in an organic solvent system in the presence of water. This intermediate can then be esterified in pyridine to form the soluble squaraine dye which can then be easily isolated from the reaction mixture. Soluble squaraine dyes are important as antihalation and acutance dyes in photothermographic products and other applications where infrared absorbing materials are needed. The invention also provides the dyes prepared according to this method.

BACKGROUND OF THE INVENTION

Squaraine dyes are known to possess photoconductive and semiconductive properties. These features have made them very attractive for various industrial applications such as xerographic photoreceptors, organic solar cells, optical recording media, antihalation dyes and acutance dyes.

The general structure of squaraine dyes is shown in dye 1. In this

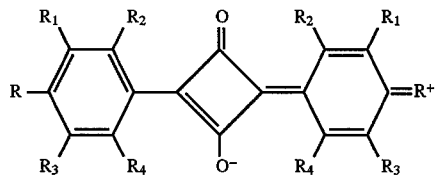

structure, R is generally N or O while $R_1$, $R_2$, $R_3$, and $R_4$ can be H, organic substituents or together form another aromatic ring.

The synthesis of squaraines (dye 1) wherein $R_1$ and $R_2$ together form a second phenyl ring has been reported. Bello describes squaraine synthesis in n-butanol and toluene with azeotropic removal of water (K. A. Bello, S. N. Corns, and J. Griffiths, *J. Chem. Soc., Chem. Commun.*, 1993, 452–454). U.S. Pat. Nos. 5,380,635 and 5,360,694 describe the synthesis of squaraine dyes in the same manner. None of these references attempts to describe optimal conditions for preparation, nor do they comment on preferred synthetic procedures.

Other synthetic procedures for squaraine dyes have been reported. These methods describe the preparation of squaraines (dye 1) wherein $R_1$, $R_2$, $R_3$, and $R_4$ are H or simple organic substituents and do not form a second aromatic ring. These dyes were first reported by H. Sprenger and W. Ziegenbein (*Angew. Chem. Internat. Ed. Engl.*, 5, 894 (1966)). Their procedure consists of heating in benzene and n-butanol, with azeotropic removal of water.

K. Law, F. C. Bailey, and L. J. Bluett (*Can. J. Chem.*, 64, 1607–1619 (1986)) describe the synthesis of this dye 1 (R=dialkylamino, $R_1$=H or a ring to R, $R_2$=H, methyl, F, ethyl, or methoxy, $R_3$=H, $R_4$=H) in either toluene or benzene with butanol, with azeotropic removal of water. They note the increase in solubility of dyes with longer alkyl chains and the decrease in the isolated yields of these dyes which "might be attributable to secondary reactions of squaraines with N,N-dialkylanilines in the reaction mixture". They also noted that "in controlled experiments that squaraines react with N,N-dialkylanilines to form colorless products", which they do not identify. They do not suggest any cures for these synthetic difficulties. Their yields of the soluble dyes were less than 9%. Column chromatography was required to purify these dyes. On the other hand, dyes with shorter alkyl chains precipitated directly from the reaction mixture and after simple filtration and solvent washing were said to be analytically pure. Yields for these less soluble dyes ranged from 9.5 to 60%.

K. Law and F. C. Bailey looked further into the synthetic procedure (*Can. J. Chem.*, 64, 2267–2273 (1986)). They contrasted two synthetic procedures, one they referred to as the "acid route" and the other the "ester route." The acid route is the traditional method and involves heating squaric acid and N,N-dialkylaniline in azeotropic solvent, including an alcohol. The ester route involves heating a diester of squaric acid and an N,N-dialkylaniline in an alcoholic solvent, and requires additional water. Heating di-n-butyl squarate and N,N-dimethylaniline in freshly dried n-butanol gave no dye. Incremental addition of water in the presence of an acid (sulfuric, oxalic, trichloroacetic, or toluenesulfonic) resulted in increased yields of dye. The highest yields were obtained in water-saturated n-butanol. Increasing the concentration of the acid (with water present) resulted in first an increase, and then a decrease in the dye yield. They suggested these results indicate that the reactive intermediate in the reaction is the half ester of squaric acid, 2. Too much acid protonates some of the N,N-dialkylaniline, reducing its reactivity.

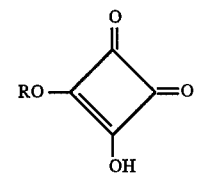

Law and Bailey also found that in the "acid route", no squaraine dye is formed if a non-hydroxylic solvent, or a secondary or tertiary alcohol is used as solvent. This is ascribed to the slower rate with which such alcohols can esterify squaric acid. They also noted that the necessity of having water in the reacting solvent in the ester route is in contrast to the acid route where water is removed continuously by an azeotropic solvent during the course of the reaction.

Law and Bailey also examined the effect of the alcohol in the "ester route." Short chain alcohols were found to give higher yields than longer chain alcohols: dimethyl squarate gave 52%, di n-propyl-47%, di n-butyl-45%, and di n-heptyl-27%. This they ascribe to an increased steric effect retarding the initial hydrolysis to 2. They also demonstrated that the ideal amount of N,N-dimethylaniline to be used is the expected 2:1 molar ratio to squarate.

Law and Bailey examined the role of water in the "ester route" by closely monitoring the boiling point of the water/saturated n-butanol reaction. They found that the initial boiling point (96° C.) slowly increased over 8 hours to 118° C. as the water/n-butanol azeotrope lost water (due to both hydrolysis of the ester and azeotropic removal from the reactor) and the medium became dry n-butanol. This removal of water from the system drives the reaction to product.

Law and Bailey further investigated the rate of addition of the N,N-dialkylaniline on the reaction. They added the N,N-dialkylaniline very slowly (over 6 to 8 hours) to the reaction mixture. They proposed that this suppresses side reactions and encourages the aniline to react with 2 (which is slowly formed from the dialkyl squarate). They said that the slow addition is especially important with highly reactive anilines (such as N,N-dimethyl-3-hydroxyaniline). Yields decreased by 30 to 50% when the aniline was added in a single batch at the beginning of the reaction.

In *J. Imaging Sci.*, 31, 172–177 (1987), K. Law and F. C. Bailey found that the squaraine dyes prepared by their "ester route" contained fewer impurities than the same dyes made by the "acid route." This resulted in better xerographic properties for the "ester route" samples.

Further work by K. Law and F. C. Bailey (*Dyes and Pigments*, 9, 85–107 (1988)), examined the synthesis of N-benzyl substituted squaraine dyes. In this case, they compared the "acid route" at 70 torr in either n-butanol and toluene, or in n-heptanol. Higher yields were found using n-heptanol, but at the expense of lowered purity. Impurities of structure 3 were found in the n-heptanol reactions. Also, some dyes could only be prepared in n-heptanol, no yield was obtained in butanol.

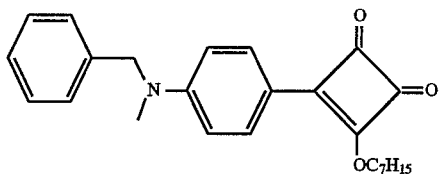

Symmetrical and unsymmetrical squaraine dyes have also been produced by an alternative route (See K. Law and F. C. Bailey, *J. Chem. Soc., Chem. Commun.*, 1990, 863–864; K. Law and F. Court Bailey, *J. Chem. Soc., Chem. Commun.*, 1991, 1156–1158; K. Law and F. C. Bailey, *J. Org. Chem.*, 57, 3278–3286 (1992)) and are summarized in the reaction scheme shown below. Here the intermediate aryl hydroxy cyclobutenedione 4 is prepared by a ketene-olefin cycloaddition. The dye is then prepared in a separate step. This synthetic scheme is covered in U.S. Pat. Nos. 4,886,722; 4,922,018; and 5,030,537.

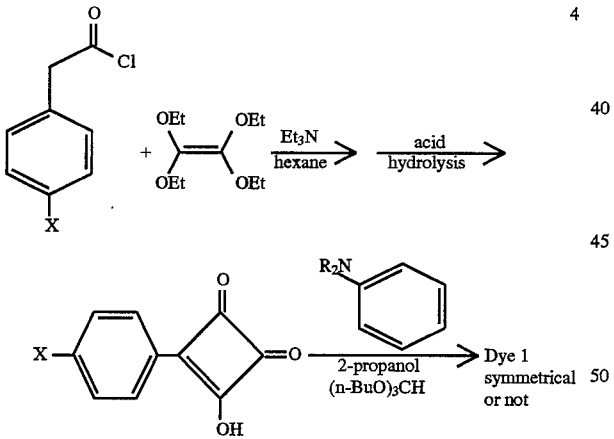

U.S. Pat. No. 4,524,219 (1985) (K. Law) is an example of the ester route and covers the reaction of a dialkylsquarate with an aniline in an alcohol with an acid catalyst. Water is not specifically mentioned in this patent, although the alcohol is referred to as "dry".

U.S. Pat. No. 4,525,592 (1985) (K. Law and F. C. Bailey) covers the same ester route as U.S. Pat. No. 4,524,219, but this time the examples indicate that water was added to the solvents.

U.S. Pat. No. 4,524,220 (1985) (K. Law) covers the reaction of squaric acid in n-butanol and benzene with an aniline, but with an added aliphatic amine. The resulting dyes are said to have improved photoconductive properties. The role of the added amine is not speculated upon.

U.S. Pat. No. 4,523,035 (1985) (J. F. Yanus) describes the use of a higher alcohol (such as heptanol) at reduced pressure with or without an acid catalyst to prepare squaraine dyes. The advantages stated are that the water separates more readily from heptanol than from butanol, that the reaction can be more readily scaled up, that competitive reactions are reduced, and that diester formation is reduced. This patent states that the butanol reactions cannot be scaled up beyond a batch size of 0.5 mole whereas the higher alcohol reactions are scaleable.

In summary, soluble squaraine dyes are known to be quite unstable in normal reaction mixtures leading to extensive decomposition during the synthesis of the squaraine system, as indicated by K. Law, F. C. Bailey, and L. J. Bluett (*Can. J. Chem.*, 64, 1607–1619 (1986)). The squaric ester route described above by K. Law and F. C. Bailey (*Can. J. Chem.*, 64, 2267–2273 (1986)), required lower alcohols, like propanol, for high yield and the exact balance of water in the reaction was critical. This type of process would be very difficult to scale up. It should be noted that there is no indication in the related art regarding the beneficial effects of additional water in the "acid route". Typically, the preparation of soluble dyes requires extensive purification of the final product by solvent extraction, recrystallization, and/or chromatography. These steps are time consuming, expensive and can generate hazardous waste.

A need exists for a simple cost effective method for the production of soluble squaraine dyes. Dyes of this type when prepared by known methods are difficult to scale up and isolate in good yield and purity.

SUMMARY OF THE INVENTION

The present invention represents a simple cost effective method for the production of soluble squaraine dyes. In the method of the present invention, we prepare a relatively insoluble intermediate squaraine dye and convert it to an organic solvent soluble dye by a very mild esterification process. The method of the present invention can be carried out in standard chemical processing equipment. The process time is relatively short, and the dye is obtained in good yield. The dye is obtained directly from the reaction mixture in pure enough form for use in most imaging constructions.

The method of the present invention can be illustrated by the following reaction scheme:

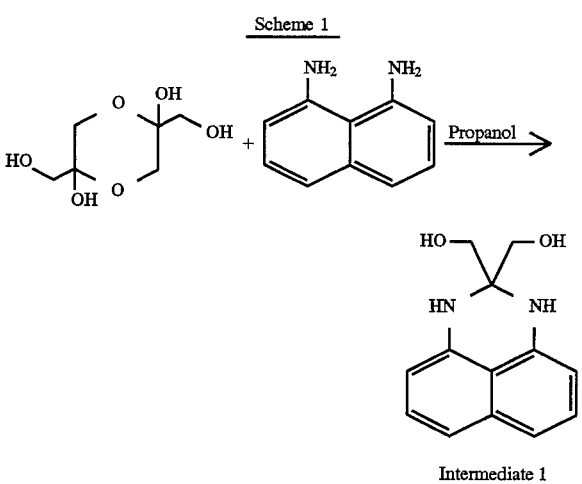

Intermediate 1

-continued
Scheme 1

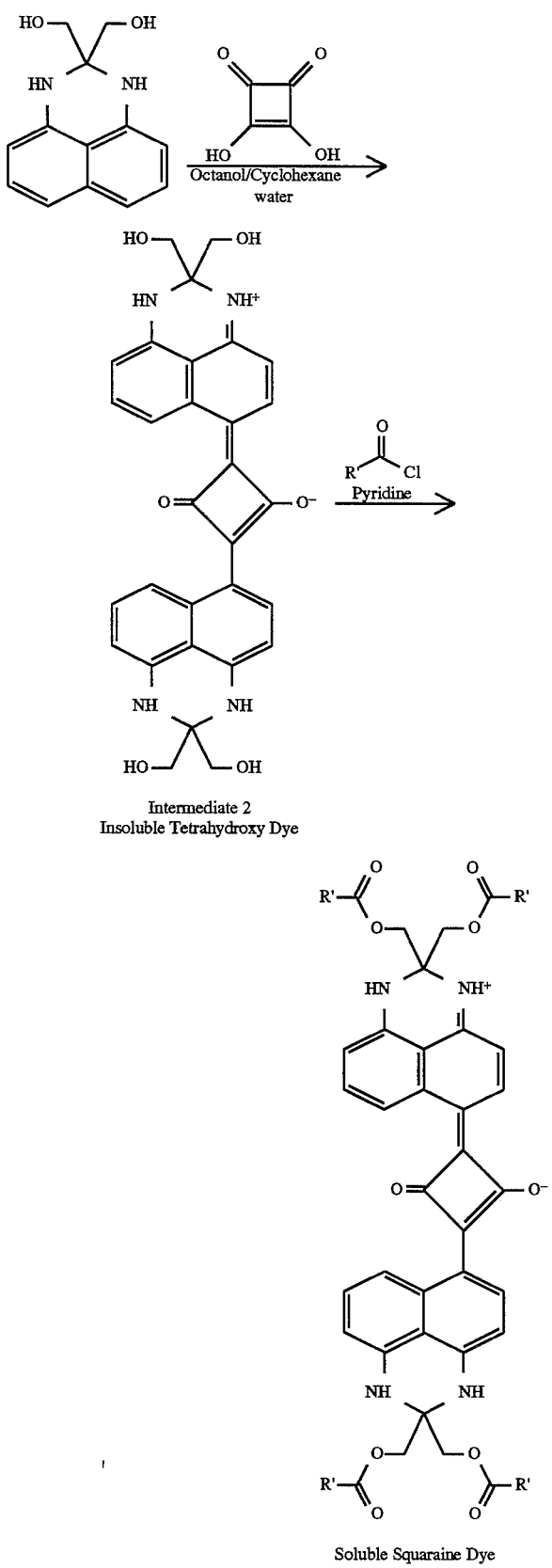

Intermediate 2
Insoluble Tetrahydroxy Dye

Soluble Squaraine Dye wherein R' is —$(CH_2)_nH$ wherein n=1 to 7.

The preparation of Intermediate 2 is done using a mixed solvent system. We have discovered that the use of a mixed solvent system described below is required to obtain the highest yields and purity of the tetrahydroxy Intermediate 2. This solvent mixture seems to provide optimal solubility for the reactants while allowing the product to precipitate before decomposition can occur. It also provides an optimal rate for the azeotropic removal of water during the reaction. The solvent system is preferably an octanol/cyclohexane mixture.

We have also discovered that a small amount of water is critical to start the reaction for the preparation of Intermediate 2. The addition of a small amount of water, or even the use of slightly wet solvents insures the start of the reaction. This is very surprising because one of the keys to obtaining high purity of this intermediate is the azeotropic removal of water during the reaction. It is important to have the water present at the very start since addition after heating will not initiate the reaction.

The Intermediate 2 dye is isolated by simply collecting it on a filter and washing it with ethanol to remove all of the octanol. Intermediate 2 can then be washed with ethyl acetate to remove the ethanol. There is then no need to dry the material. It is used directly in the esterification step.

The squaraine dye is made soluble in conventional organic coating solvents (methyl ethyl ketone, or acetone for example) by the incorporation of multiple long alkyl chains. The process of the present invention incorporates solubilizing alkyl groups in the final step using very mild low temperature esterification conditions and a very efficient isolation procedure.

The esterification of Intermediate 2 with an aliphatic acid chloride comprising about 2 to about 8 carbons is conveniently carried out at fairly high yields using pyridine as a solvent and base. It was stirprising to find that, while the squaraine dyes are very susceptible to attack by nitrogen bases such as triethyl amine which is commonly used in these types of esterifications, they are completely stable in pyridine at ambient temperatures or below. While the reaction can be done at room temperature (about 20° to 30° C.) in this system, we obtained higher purlties and higher yields at lower temperatures (below about 10° C.).

We also discovered an extremely effective precipitation procedure to isolate pure dye directly from the reaction mixture so no further purification is needed even for use in imaging constructions. We discovered that by adding ethyl acetate followed by the addition of water and enough hydrochloric acid to convert all of the pyridine to its water soluble hydrochloride salt, the squaraine dye precipitated in extremely pure form. Preferably the mixture is warmed to about 20°–30° C. The dye is then collected by filtration followed by washing with methanol, and air drying.

The present invention thus provides a novel method of making squaraine dyes. The invention provides a method of making a compound comprising the steps of:

(a) forming a first mixture comprising:

(I) a compound of the structure

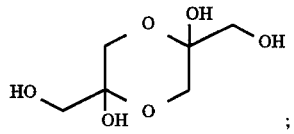

;

(II) a compound of the structure

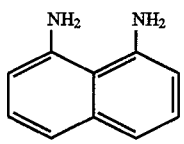

, wherein the molar ratio of the compound of (a)(I) to the compound of (a)(II) is 0.5:1 or greater; and (III) about 50 to about 90 percent by weight of a solvent selected from the group consisting of ethanol, n-propanol, isopropanol, and mixtures thereof, based upon the total weight of the first mixture;

wherein the first mixture is free of acid catalyst;

(b) heating the first mixture to allow the first mixture to react in order to form a first intermediate of the formula

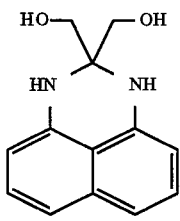

, wherein the first mixture is agitated during step (b);

(c) cooling the mixture of step (b) to a temperature below about 30° C. followed by isolating the first intermediate by filtration from the mixture of step (b);

(d) washing the first intermediate with a solvent selected from the group consisting of ethanol, propanol, isopropanol, and mixtures thereof;

(e) forming a second mixture, wherein the second mixture comprises:

(I) the first intermediate;

(II) squaric acid;

wherein the molar ratio of the first intermediate to squaric acid is about 2:1 to about 1.7:1;

(III) a solvent selected from the group consisting of heptanol, octanol, and mixtures thereof;

(IV) a cosolvent selected from the group consisting of n-hexane, cyclohexane, heptane, and mixtures thereof, wherein the volume ratio of the solvent of (e)(III) to the cosolvent of (e)(IV) ranges from about 60:40 to about 90:10;

wherein the total amount of the solvent of (e)(III) plus the cosolvent of (e)(IV) present in the second mixture ranges from about 60 to about 95 percent by weight based upon the total weight of the second mixture;

(V) water, wherein the amount of water added in step (e) is sufficient to initiate the reaction of the first intermediate and squaric acid upon heating in step (f);

(f) heating, with agitation, the second mixture to reflux until consumption of the first intermediate ceases in order to form a second intermediate of the formula

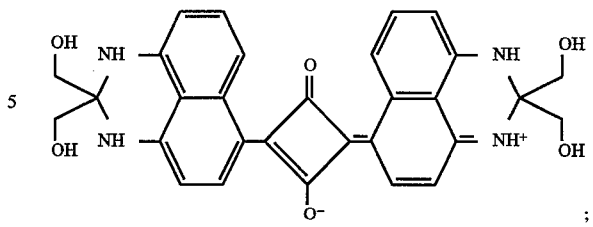

;

optionally removing water from the mixture via azeotrope during step (f);

(g) cooling the second mixture to a temperature of about 10 to about 40 degrees C;

(h) isolating the second intermediate by filtration from the mixture of step (g);

(i) washing the second intermediate in ethanol to remove any remaining octanol or heptanol, followed by washing the second intermediate in ethyl acetate to remove any remaining ethanol;

(j) forming a third mixture comprising:

(I) the second intermediate; and (II) pyridine;

wherein about 15 to about 40 molar equivalents of pyridine are present in the third mixture based on the second intermediate;

(k) forming a fourth mixture by adding, with agitation, about 4 to about 6 molar equivalents of an aliphatic acid chloride comprising about 2 to about 8 carbon atoms, based on the second intermediate, to the third mixture; wherein the fourth mixture is not allowed to reach a temperature greater than about 50 degrees C by virtue of one or both of the following (I) cooling the mixture; (II) controlling the rate at which the aliphatic acid chloride is added; in order to form a compound of the formula

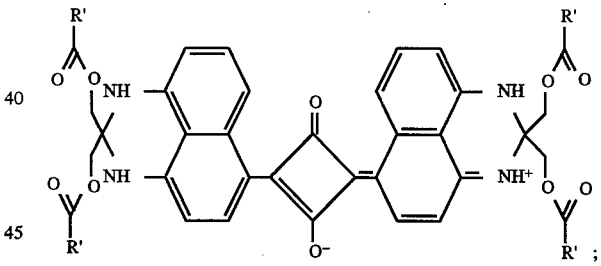

wherein R' is —$(CH_2)_n$H wherein n=1 to 7.

wherein essentially anhydrous conditions are maintained throughout steps (j) and (k);

(l) isolating the compound of step (k) by adding an acetate ester selected from the group consisting of ethyl acetate, isopropyl acetate, amyl acetate, methyl acetate, propyl acetate, butyl acetate, and mixtures thereof and an aqueous HCl solution to the fourth mixture in order to form a final mixture from which the compound precipitates out, wherein the molar equivalent of the aliphatic acid chloride included in step (k) plus the molar equivalent of HCl included in step (l) approximately equals the molar equivalent of pyridine included in step (j);

wherein the weight ratio of acetate ester plus water to pyridine is about 3:1 to about 8:1; and wherein the weight ratio of acetate ester to water is about 0.5:1 to about 2:1;

(m) isolating the compound by filtration from the final mixture which is optionally warmed to solubilize any impurities prior to filtration; and (n) washing the compound with ethyl acetate followed by methanol in order to purify the compound.

DETAILED DESCRIPTION OF THE INVENTION

As indicated previously the first step of the method of the invention involves forming a first mixture comprising:

(I) a compound of the structure

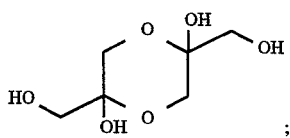

(II) a compound of the structure

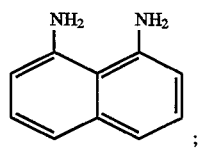

wherein the molar ratio of the compound of (I) to the compound of (II) is 0.5:1 or greater (preferably about 0.5:1 to 0.7:1); and (III) about 50 to about 90 percent by weight of a solvent selected from the group consisting of ethanol, n-propanol, isopropanol, and mixtures thereof, based upon the total weight of the first mixture;

wherein the first mixture is free of acid catalyst.

The first mixture includes a solvent selected from the group consisting of ethanol, n-propanol, isopropanol, and mixtures thereof. The purpose of this solvent is to provide solubility for the reactants and furthermore cause the desired product to crystallize upon cooling to facilitate the isolation. These solvents also provide for an ideal reflux temperature to facilitate the reaction.

As indicated above the first mixture must be free of acid catalyst. For example, the use of an acid catalyst such as para-toluenesulfonic acid to accelerate the reaction would have adverse effects later in the process causing the final dye mixture to become nearly impossible to filter.

In the second step the first mixture is heated, with agitation, to reflux in order to form a first intermediate of the formula

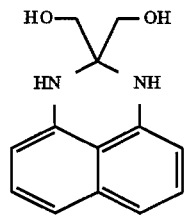

The first mixture is typically heated to a temperature range of about 30 degrees C. to about 150 degrees C., preferably about 60 degrees C. to about 100 degrees C., and most preferably about 75 degrees C. to about 100 degrees C. The reaction typically takes place in about 0.5 to about 6 hours, more typically about 1 to about 3 hours.

The next step involves cooling the first mixture to a temperature below about 30° C., preferably about 20° to about 25° C., followed by isolating the first intermediate by filtration. This can be accomplished by a number of methods including but not limited to vacuum filtration and centrifuge filtration. It is important to cool to below 30° C. to assure complete crystallization of Intermediate 1 from the reaction mixture.

Next, the first intermediate is washed with a solvent selected from the group consisting of ethanol, propanol, isopropanol, and mixtures thereof. These solvents work well due to the low solubility of the product in them, while traces of starting materials present would be soluble and thus removed.

The next step involves forming a second mixture, wherein the second mixture comprises: the first intermediate; squaric acid; a solvent selected from the group consisting of heptanol, octanol, and mixtures thereof; a cosolvent selected from the group consisting of n-hexane, cyclohexane, heptane, and mixtures thereof; and water.

It is critical in this step that the molar ratio of the first intermediate to squaric acid is about 2:1 to about 1.7:1. Excess squaric acid would retard the reaction which would lead to more decomposition of the desired product.

The solvent is selected from the group consisting of heptanol, octanol, and mixtures thereof. The use of these solvents enables one to form the required monoester of squaric acid, and at the same time facilitate the removal of water from the reaction mixture. Preferably the solvent is octanol. Lower alcohols such as $C_{1-6}$ are not suitable, as such lower alcohols would be very difficult to remove from the product. Long drying times (several days) at elevated temperature (200 degrees C.) would be required to remove these lower alcohols. Such drying conditions are undesirable due to the observed thermal instability of Intermediate 2 prepared by such a method.

It is also important to use a cosolvent selected from the group consisting of n-hexane, cyclohexane, heptane, and mixtures thereof. These cosolvents serve to create an azeotrope with water and the solvent (octanol and/or heptanol) at a temperature high enough to provide a convenient rate of reaction but low enough to prevent decomposition of the product. Additionally, these are non-solvents for the product, ensuring product precipitation. If cosolvents such as toluene were used the mixture would have a higher azeotrope temperature resulting in lower purities. Preferably the cosolvent is cyclohexane in order to obtain highest yields and purities.

It is also critical that the volume ratio of the solvent to the cosolvent in this step ranges from about 60:40 to about 90:10. It is important to maintain this range as this is the range in which the azeotrope temperature is high enough to allow reaction but low enough to cause little decomposition of the product. If the volume ratio fell below about 60:40 the reaction temperature would be too low for reaction to occur in a reasonable amount of time. If the volume fell above the ratio of about 90:10, purity would drop due to the higher azeotrope temperature. Preferably the volume ratio of the solvent to the cosolvent ranges from about 65:35 to about 80:20 for reasons of highest yield and purity.

It is also critical that the total amount of the solvent plus the cosolvent present in the second mixture ranges from about 60 to about 95 weight percent based upon the total weight of the second mixture for the following reasons. Amounts of solvent outside this range result in problems related to material handling (stirring, filtration, etc.).

Preferably the total amount of solvent plus cosolvent present in the second mixture ranges from about 75% to about 85% based upon the total weight of the second mixture for reasons of optimum yield and purity.

It is also critical that about 0.05 to about 3 percent by weight water, based on the total weight of the solvent plus the cosolvent be included during this step. If the water were not present the reaction would fail to start. Preferably the amount of water included in this step is about 0.1 to about 0.5 percent by weight based on the total weight of the solvent plus the cosolvent.

The next step involves heating the second mixture to reflux, with agitation, until consumption of the first intermediate ceases in order to form a second intermediate of the formula

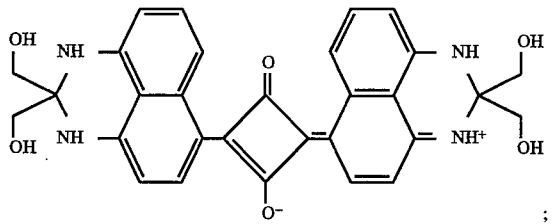

;

while optionally removing water from the mixture via azeotrope during this step in order to provide higher yields and purity. It is thus preferred to remove water during this step. Typically this procedure takes about 1 to about 4 hours, more typically about 3 hours.

The next step involves cooling the second mixture to a temperature of about 10 to about 40 degrees C. which is a convenient and relatively safe temperature for handling the mixture under normal circumstances.

The next step involves isolating the second intermediate by filtration from the mixture. This can be done by a number of methods such as, for example, vacuum filtration and centrifuge filtration.

The next step involves washing the second intermediate with ethanol to remove any remaining octanol and/or heptanol. Ethanol washing is convenient to remove octanol and/or heptanol. Ethanol provides a low cost, low toxicity solvent which can easily be removed by ethyl acetate. The next step involves washing the second intermediate in ethyl acetate to remove any remaining ethanol. It is important to use ethyl acetate because ethyl acetate works well to remove all of the ethanol and will not interfere in the next step. It is important to remove all alcohols because they would react in the next step and lower the yield. If ethyl acetate is used it is not necessary to dry the second intermediate prior to use in the next step. It is advantageous to avoid a drying step due to the thermal instability of the second intermediate.

In the next two steps essentially anhydrous conditions are maintained throughout, as the presence of water would decrease the yield. It is important to minimize or eliminate water present in order to minimize losses due to hydrolysis.

The purity of Intermediate 2 prepared according to the invention typically is at least about 65%, preferably at least 80% as determined by NMR.

The next step involves forming a third mixture comprising the second intermediate and pyridine, wherein about 15 to about 40 molar equivalents of pyridine are present in the third mixture based on the second intermediate. If less than about 15 molar equivalents were present the reaction mixture would become too thick to stir effectively. If greater than about 40 molar equivalents were present precipitation of the final dye would be incomplete. It is important that the second intermediate be well dispersed in the pyridine solvent. This can be achieved by careful addition of the intermediate to the pyridine under high agitation or by the use of a homogenizer or similar equipment. Preferably about 20 to about 30 molar equivalents of pyridine are present in the third mixture based upon the second intermediate in order to optimize mixing and precipitation.

The next step involves forming a fourth mixture by adding, with agitation, about 4 to about 6 molar equivalents of an aliphatic acid chloride (preferably n-hexanoyl chloride) based on the second intermediate to the third mixture; wherein the fourth mixture is not allowed to reach a temperature greater than about 50 degrees C by virtue of one or both of the following: (I) cooling the mixture; (II) controlling the rate at which the aliphatic acid chloride is added; in order to form a compound of the formula

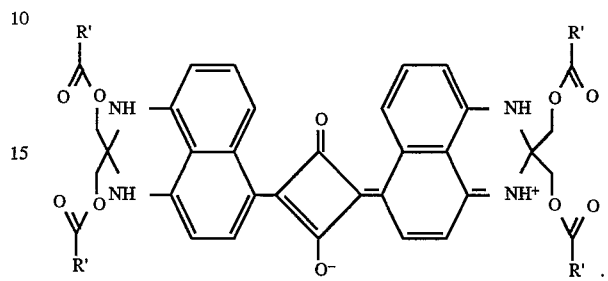

wherein R' is defined above. Preferably R' is $C_5H_{11}$.

If greater than about 6 molar equivalents of aliphatic acid chloride were added the yield could decrease greatly. Preferably the molar equivalents of aliphatic acid chloride in the fourth mixture ranges from about 4.6 to about 5 for reasons of optimum yield.

It is important that the fourth mixture not be allowed to reach a temperature greater than about 50 degrees C. in order to avoid decomposition of the product, preferably not greater than about 10 degrees C. to further minimize decomposition.

The next step involves isolating the compound by adding an acetate ester selected from the group consisting of ethyl acetate, isopropyl acetate, amyl acetate, butyl acetate, propyl acetate, methyl acetate, and mixtures thereof and an aqueous HCl solution to the fourth mixture in order to form a final mixture from which the compound precipitates. It is critical that the molar equivalent of aliphatic acid chloride included in a previous step plus the molar equivalent of HCl included in this step approximately equal (preferably equal) the molar equivalent of pyridine. If the HCl is used in an amount insufficient to neutralize all the pyridine, the pyridine will be difficult to remove.

It is also critical that the weight ratio of acetate ester plus water to pyridine is about 3:1 to 8:1 and that the weight ratio of acetate ester to water is about 0.5:1 to 2:1. If these ratios are not satisfied the product will not precipitate in good yields. Preferably, in this step the ratio of acetate ester plus water to pyridine is about 4:1 to 5:1, and the ratio of acetate ester to water is about 1: 1 to about 1.5:1. It is preferred to warm the mixture to solubilize the impurities prior to filtration, preferably about 10 to about 30 degrees, and most preferably about 20 to about 30 degrees C.

The next step involves isolating the compound by filtration. This can be done by a number of methods including but not limited to vacuum filtration and centrifuge filtration.

The next step involves washing the compound with an acetate ester selected from the group consisting of ethyl acetate, isopropyl acetate, amyl acetate, methyl acetate, propyl acetate, butyl acetate, and mixtures thereof, followed by methanol in order to purify the compound. The acetate effectively removes byproducts from the reactants. Methanol effectively removes pyridine hydrochloride.

The purity of the compound prepared according to the invention typically is at least about 80 percent of theoretical, preferably at least about 90 percent as determined by NMR or ultraviolet spectroscopy.

The reaction vessel and conditions under which the compound is made can vary but typically glass vessels capable of heating, cooling, reflux and azeotropic removal of water are used. The yields of dye obtained via the method of the invention are typically from about 40 percent or greater, preferably about 85 percent or greater, based upon the theoretical yield.

EXAMPLES

The following examples further illustrate but do not limit the present invention. All parts, percentages, ratios, etc. are by weight unless indicated otherwise.

EXAMPLE 1

Preparation of Intermediate 1

477 g (3.015 moles) of 1,8-diaminonaphthalene, 295 g (1.635 moles) of 1,3-dihydroxyacetone dimer, and 2.7 liters of 1-propanol were combined in a 5 liter glass flask fitted with a mechanical stirrer and reflux condenser. The resulting mixture was then heated to reflux. After 1 hour at reflux, the mixture was cooled to 25° C. The product which crystallized from the reaction mixture upon cooling was collected via vacuum filtration and washed with 500 ml of 1-propanol. The tan solid was then recrystallized from another 2 liters of 1-propanol, filtered via vacuum filtration and air dried. The yield was 528 g (76% yield).

EXAMPLES 2–5

Preparation of Intermediate 2. Investigation of Solvent Effects on Yield and Purity of Intermediate 2.

General procedure: A mixture of 1.00 g (4.35 mmol) of Intermediate 1, 0.248 g (2.17 mmol) of squaric acid, 5 ml of 1-octanol, and 2 ml of the cosolvent (see Table 1 ) was heated with magnetic stirring at reflux with a Dean-Stark trap under nitrogen for 1 hour. After cooling to room temperature (about 25 degrees C.), the product was filtered off, washed with ethanol, and dried. The purity of the product was determined by proton NMR analysis in DMSO-$d_6$ using 2,3,5-triiodobenzoic acid as an internal standard. The crude yield, purity, and actual yield are recorded in Table 1.

TABLE 1

| Example | Cosolvent | Cosolvent Boiling Point (°C.) | Crude Yield (%) | Purity (%) | Actual Yield (%) |
| --- | --- | --- | --- | --- | --- |
| 2 | toluene | 110 | 86 | 75 | 64 |
| 3 | heptane | 98 | 90 | 80 | 72 |
| 4 | cyclohexane | 81 | 96 | 85 | 82 |
| 5 | hexane | 69 | 92 | 87 | 80 |

EXAMPLE 6

Esterification of Intermediate 2 (Example 2)

10.00 g of crude intermediate 2 as obtained from Example 2, 37 ml of pyridine and 11 ml of ethyl acetate were combined with mechanical stirring in a 500 ml flask under nitrogen. Next, 11.6 ml of hexanoyl chloride were added dropwise to this mixture over 5 minutes. The mixture was cooled during the hexanoyl chloride addition using a water bath. After 1 hour, 75 ml of ethyl acetate was added, the mixture stirred for 20 minutes, and then cooled in an ice/water bath. 38.9 g of concentrated hydrochloric acid in 50.7 ml of water were added slowly, keeping the temperature below 17° C. The mixture was warmed to room temperature for 40 minutes and the product was vacuum filtered off, washed with 300 ml of water, partially air dried, stirred with 85 ml of methanol for 38 min, vacuum filtered, and dried. The resulting yield was 57%.

EXAMPLE 7

Esterification of Intermediate 2 (Example 4)

10.00 g of crude Intermediate 2 as obtained from Example 4, 37 ml of pyridine, and 11 ml of ethyl acetate were combined with mechanical stirring in a 500 ml flask under nitrogen. Next, 11.6 ml of hexanoyl chloride were added dropwise over 5 min. The mixture was cooled during the hexanoyl chloride addition using a water bath. After 1 hour, 75 ml of ethyl acetate was added, the mixture stirred for 20 min, and then cooled in an ice/water bath. 38.9 g of concentrated hydrochloric acid in 50.7 ml of water were added slowly, keeping the temperature below 17° C. The mixture was warmed to room temperature for 40 min, and the product was vacuum filtered off, washed with 300 ml of water, partially air dried, stirred with 85 ml of methanol for 38 min, vacuum filtered, and dried. The resulting yield was 64%. In comparison with Example 6, the purer lot of Intermediate 2 used in this example gave the higher yield of final dye product.

EXAMPLE 8–12

Preparation of Intermediate 2. Comparison of Solvent Ratio and Added Water

General procedure: 20 g of Intermediate 1 (0.087 moles), 4.95 g of squaric acid (0.0434 moles), cyclohexane, toluene, and water charges indicated in Table 2 were combined in a 500 ml flask fitted with a mechanical stirrer, a Dean-Stark trap and a reflux condenser. The mixture was heated to reflux and was held at reflux for a total of 1 hour. At the end of the reflux period, the mixture was cooled to room temperature (about 25° C.). The solid Intermediate 2 was collected by vacuum filtration, washed with ethanol until the washings were light yellow, and air dried overnight. The results are summarized in Table 2. Note that the octanol was not dried, so water was present in all reactions in this table.

TABLE 2

| Example | Cyclo-hexane (ml) | Octanol (ml) | Added Water (ml) | Temp. (°C.) | Yield (g) | Purity (%) |
| --- | --- | --- | --- | --- | --- | --- |
| 8 | 53 | 80 | 1 | 95.5 | 10.3 | 63 |
| 9 | 27 | 107 | 1 | 111.5 | 19.9 | 72 |
| 10 | 53 | 80 | 0 | 97.9 | 15 | 80 |
| 11 | 27 | 107 | 0 | 114.5 | 21 | 74 |
| 12 | 40 | 93 | 0.5 | 110 | 21.3 | 79 |

EXAMPLE 13

Preparation of Intermediate 2 Without Azeotropic Water Removal 20 g of Intermediate 1 (0.087 moles), 4.95 g of squaric acid (0.0434 moles), 40 ml of cyclohexane, and 93 ml of octanol were combined in a 500 ml flask fitted with a mechanical stirrer, and a reflux condenser. The mixture was heated to reflux and held at reflux for a total of 1 hour. At the end of the reflux period, the mixture was cooled to room temperature (about 25° C.). The solid Intermediate 2 was collected by vacuum filtration, washed with ethanol until the washings were light yellow, and air dried overnight. The resulting yield was 17.7 g and the purity by proton NMR was only 68%. This illustrates that the removal of water from the reaction mixture via azeotropic distillation is important to obtaining high purity.

EXAMPLE 14

Intermediate 2 preparation 50 g of Intermediate 1 (from Example 1), 12.38 g of squaric acid, 100 ml of cyclohexane, 232.5 ml of octanol and 1.0 ml of water were combined in a 1 liter flask fitted with a thermometer, mechanical stirrer, and a Dean Stark trap. The mixture was heated to reflux. After 3 hours, the accumulation of water in the trap had stopped. The reaction was cooled to room temperature (about 25 degrees C.). The solid product collected on a Buchner funnel, washed with 900 ml of ethanol and 900 ml of ethyl acetate and sealed in a bottle. The dry yield was calculated after air drying a sample overnight to be 95.04% and NMR analysis indicated that it was 82% pure.

EXAMPLE 15

Soluble Dye Preparation Using 5.0 Molar Equivalents of Hexanoyl Chloride 25 g (0.046 moles) of Intermediate 2 (prepared similar to, but not identical to, Example 14, and having a purity of 66%) and 90 g of pyridine (1.137 moles) were combined in a 1 liter flask under a dry nitrogen atmosphere. The mixture was cooled to <5° C. with an ice bath. 31.2 g (0.232 moles) of hexanoyl chloride was added slowly keeping the temperature below 10° C. The total addition time was 1 hour. After the addition was complete, stirring was continued for 1 hour at 5° C. 243 g of ethyl acetate were then added. A premix of 126 g of water and 91 g of 37% hydrochloric acid was then slowly added keeping the temperature below 10° C. After this addition was complete the mixture was stirred for 20 minutes at 5° C. The solid product was collected via filtration. The resulting solid was washed on the filter with 100 ml of ethyl acetate and 400 ml of methanol. After air drying, the yield was 57%, which when taking the purity of the Intermediate 2 (66%) into account the true yield was 86%. The final dye was 83% pure with 11% unreacted Intermediate 2.

EXAMPLE 16

Soluble Dye Preparation Using 5.6 Molar Equivalents of Hexanoyl Chloride 25 g (0.046 moles) of Intermediate 2 (prepared similar to, but not identical to, Example 14, and having a purity of 66%) and 90 g of pyridine (1.137 moles) were combined in a 1 liter flask. The mixture was cooled to <5° C. with an ice bath. 35.0 g (0.260 moles) of hexanoyl chloride were slowly added keeping the temperature below 10° C. The total addition time was 1 hour. After the addition was complete, stirring was continued for 1 hour at 5° C. 243 g of ethyl acetate were then added. A premix of 126 g of water and 91 g of 37% hydrochloric acid was then slowly added keeping the temperature below 10° C. After this addition was complete the mixture was stirred 20 minutes at 5° C. The solid product was then collected via filtration. The resulting solid was washed on the filter with 100 ml of ethyl acetate and 400 ml of methanol. After air drying, the yield was 42%, which when taking the purity of the Intermediate 2 into account (66%) the true yield was 57%. The final dye was 92% pure with 2% unreacted Intermediate 2.

While this invention has been described in connection with specific embodiments, it should be understood that it is capable of further modification. The claims herein are intended to cover those variations which one skilled in the art would recognize as the chemical equivalent of what has been described here.

We claim:

1. A method of making a compound comprising the steps of:
   (a) forming a first mixture comprising:
      (I) a compound of the structure

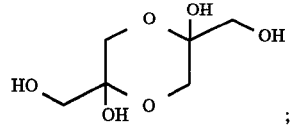

(II) a compound of the structure

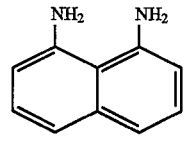

wherein the molar ratio of the compound of (a)(I) to the compound of (a)(II) is 0.5:1 or greater; and
      (III) about 50 to about 90 percent by weight of a solvent selected from the group consisting of ethanol, n-propanol, isopropanol, and mixtures thereof, based upon the total weight of the first mixture;
   wherein the first mixture is free of acid catalyst;
   (b) heating the first mixture to allow the first mixture to react in order to form a first intermediate of the formula

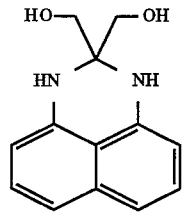

wherein the first mixture is agitated during step (b);
   (c) cooling the mixture of step (b) to a temperature below about 30° C. followed by isolating the first intermediate by filtration from the mixture of step (b);
   (d) washing the first intermediate with a solvent selected from the group consisting of ethanol, propanol, isopropanol, and mixtures thereof;
   (e) forming a second mixture, wherein the second mixture comprises:
      (I) the first intermediate;
      (II) squaric acid;
   wherein the molar ratio of the first intermediate to squaric acid is about 2:1 to about 1.7:1;
      (III) a solvent selected from the group consisting of heptanol, octanol, and mixtures thereof;
      (IV) a cosolvent selected from the group consisting of n-hexane, cyclohexane, heptane, and mixtures thereof;
   wherein the volume ratio of the solvent of (e)(III) to the cosolvent of (e)(IV) ranges from about 60:40 to about 90:10;
   wherein the total amount of the solvent of (e)(III) plus the cosolvent of (e)(IV) present in the second mixture ranges from about 60 to about 95 percent by weight based upon the total weight of the second mixture;

(V) water, wherein the amount of water added in step (e) is sufficient to initiate the reaction of the first intermediate and squaric acid upon heating in step (f);

(f) heating, with agitation, the second mixture to reflux until consumption of the first intermediate ceases in order to form a second intermediate of the formula

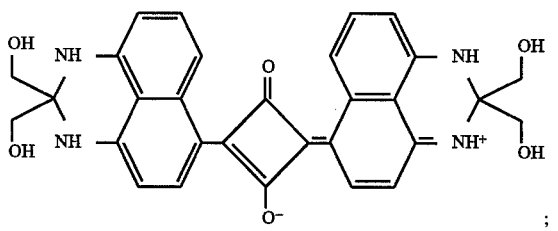

optionally removing water from the mixture via azeotrope during step (f);

(g) cooling the second mixture to a temperature of about 10 to about 40 degrees C.;

(h) isolating the second intermediate by filtration from the mixture of step (g);

(i) washing the second intermediate in ethanol to remove any remaining octanol or heptanol, followed by washing the second intermediate in ethyl acetate to remove any remaining ethanol;

(j) forming a third mixture comprising:
(I) the second intermediate; and
(II) pyridine;
wherein about 15 to about 40 molar equivalents of pyridine are present in the third mixture based on the second intermediate;

(k) forming a fourth mixture by adding, with agitation, about 4 to about 6 molar equivalents of an aliphatic acid chloride comprising about 2 to about 8 carbon atoms, based on the second intermediate, to the third mixture; wherein the fourth mixture is not allowed to reach a temperature greater than about 50 degrees C. by virtue of one or both of the following (I) cooling the mixture; (II) controlling the rate at which the aliphatic acid chloride is added; in order to form a compound of the formula

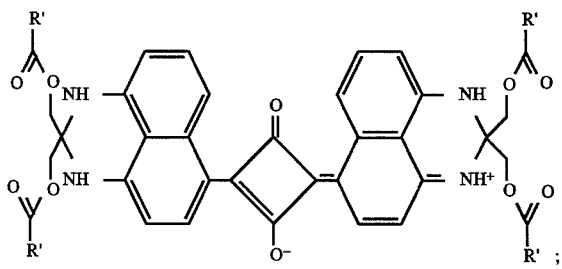

wherein R' is —$(CH_2)_n$H wherein n=1 to 7.

wherein essentially anhydrous conditions are maintained throughout steps (j) and (k);

(l) isolating the compound of step (k) by adding an acetate ester selected from the group consisting of ethyl acetate, isopropyl acetate, amyl acetate, methyl acetate, propyl acetate, butyl acetate, and mixtures thereof and an aqueous HCl solution to the fourth mixture in order to form a final mixture from which the compound precipitates, wherein the molar equivalent of the aliphatic acid chloride included in step (k) plus the molar equivalent of HCl included in step (l) approximately equals the molar equivalent of pyridine included in step (j); wherein the weight ratio of acetate ester plus water to pyridine is about 3:1 to about 8:1; and
wherein the weight ratio of acetate ester to water is about 0.5:1 to about 2:1;

(m) isolating the compound by filtration from the final mixture which is optionally warmed to solubilize any impurities prior to filtration; and (n) washing the compound with ethyl acetate followed by methanol in order to purify the compound.

2. The method of claim 1 wherein the amount of water included in step (e) is about 0.05 to about 3 percent by weight based on the total weight of the solvent of (e)(III) plus the cosolvent of (e)(IV).

3. The method of claim 1 wherein the amount of water included in step (e) is about 0.1 to about 3 percent by weight based on the total weight of the solvent of (e)(III) plus the cosolvent of (e)(IV).

4. The method of claim 1 wherein the amount of water included in step (e) is about 0.1 to about 0.5 percent by weight based on the total weight of the solvent of (e)(III) plus the cosolvent of (e)(IV).

5. The method of claim 1 wherein the molar ratio of the compound of (a)(I) to the compound of (a)(II) is about 0.5:1 to 0.7:1.

6. The method of claim 1 wherein about 70 to about 80 percent by weight of a solvent selected from the group consisting of ethanol, n-propanol, isopropanol, and mixtures thereof is present in the first mixture, based upon the total weight of the first mixture.

7. The method of claim 1 wherein the solvent of (e)(III) is octanol.

8. The method of claim 1 wherein the cosolvent of (e)(IV) is cyclohexane.

9. The method of claim 1 wherein about 20 to about 30 molar equivalents of pyridine are present in the third mixture based upon the second intermediate.

10. The method of claim 1 wherein the volume ratio of the solvent of (e)(III) to the cosolvent of (e)(IV) ranges from about 65:35 to about 80:20.

11. The method of claim 1 wherein the total amount of solvent of (e)(III) plus cosolvent of (e)(IV) present in the second mixture ranges from about 75 to about 85 percent based upon the total weight of the second mixture.

12. The method of claim 1 wherein the molar equivalents of aliphatic acid chloride in the fourth mixture range from about 4.6 to about 5.6.

13. The method of claim 1 wherein in step (l) the ratio of acetate ester plus water to pyridine is about 4:1 to 5:1, and the ratio of acetate ester to water is about 1:1 to about 1.5:1.

14. The method of claim 1 wherein the fourth mixture is not allowed to reach a temperature greater than about 10 degrees C.

15. The compound formed according to the method of claim 1.

16. The method of claim 1 wherein water is removed from the mixture via azeotrope during step (f).

17. The method of claim 1 wherein the final mixture is warmed to a temperature of about 10 to about 30 degrees to solubilize any impurities prior to filtration.

18. The method of claim 1 wherein the final mixture is warmed to a temperature of about 20 to about 30 degrees C. to solubilize any impurities prior to filtration.

19. A method of making a compound comprising the steps of:

(a) forming a first mixture comprising:
(I) a compound of the structure

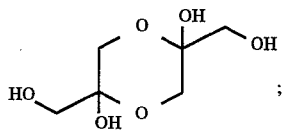

(II) a compound of the structure

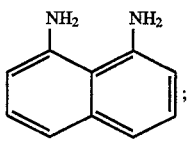

and (III) a solvent selected from the group consisting of ethanol, n-propanol, isopropanol, and mixtures thereof;
wherein the first mixture is free of acid catalyst;
(b) heating the first mixture to allow the first mixture to react in order to form a first intermediate of the formula

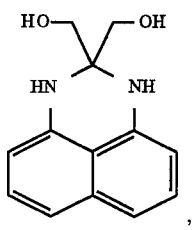

wherein the first mixture is agitated during step (b);
(c) cooling the mixture of step (b) to a temperature below about 30° C. followed by isolating the first intermediate by filtration from the mixture of step (b);
(d) washing the first intermediate with a solvent selected from the group consisting of ethanol, propanol, isopropanol, and mixtures thereof;
(e) forming a second mixture, wherein the second mixture comprises:
(I) the first intermediate;
(II) squaric acid;
wherein the molar ratio of the first intermediate to squaric acid is about 2:1 to about 1.7:1;
(III) a solvent which is octanol;
(IV) a cosolvent which is cyclohexane;
wherein the volume ratio of the solvent of (e)(III) to the cosolvent of (e)(IV) in the second mixture ranges from about 65:35 to about 80:20;

wherein the total amount of the solvent of (e)(III) plus the cosolvent of (e)(IV) present in the second mixture ranges from about 75 to about 85 percent by weight based upon the total weight of the second mixture;
(V) about 0.1 to about 0.5 percent by weight water, based on the total weight of the solvent of (e)(III) plus the cosolvent of (e)(IV);
(f) heating the second mixture to reflux until consumption of the first intermediate ceases in order to form a second intermediate of the formula

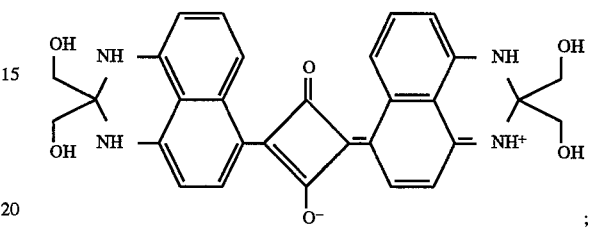

wherein water is removed from the mixture via azeotrope during step (f);
(g) cooling the second mixture to a temperature of about 10 to about 40 degrees C.;
(h) isolating the second intermediate by filtration from the mixture of step (g);
(i) washing the second intermediate in ethanol to remove any remaining octanol, followed by washing the second intermediate in ethyl acetate to remove any remaining ethanol;
(j) forming a third mixture comprising:
(I) the second intermediate; and
(II) pyridine;
wherein about 20 to about 30 molar equivalents of pyridine are present in the third mixture based on the second intermediate;
(k) forming a fourth mixture by adding, with agitation, about 4.6 to about 5 molar equivalents of n-hexanoyl chloride based on the second intermediate to the third mixture; wherein the fourth mixture is not allowed to reach a temperature greater than about 10 degrees C. by virtue of one or both of the following (I) cooling the mixture; (II) controlling the rate at which the hexanoyl chloride is added; in order to form a compound of the formula

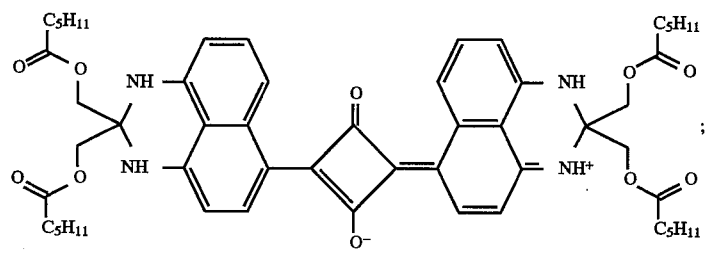

wherein essentially anhydrous conditions are maintained throughout steps j) and (k);
(l) isolating the compound of step (k) by adding an acetate ester selected from the group consisting of ethyl acetate, isopropyl acetate, and mixtures thereof and an aqueous HCl solution to the fourth mixture to form a final mixture from which the compound precipitates, wherein the molar equivalent of hexanoyl chloride included in step (i) plus the molar equivalent of HCl included in step (l) approximately equals the molar equivalent of pyridine included in step (j);

wherein the weight ratios of acetate plus water to pyridine is about 4:1 to 5:1 and wherein the weight ratio of acetate ester to water is about 1:1 to 1.5:1;

(m) isolating the compound by filtration from the final mixture, wherein the final mixture is warmed to a temperature of about 20 to about 30 degrees C. to solubilize any impurities prior to filtration;

(n) washing the compound with ethyl acetate followed by methanol in order to purify the compound.

20. The compound formed according to the method of claim 19.

* * * * *